United States Patent [19]

Mooring

[11] Patent Number: 5,634,201
[45] Date of Patent: May 27, 1997

[54] COMMUNICATIONS VISOR

[76] Inventor: Jonathon E. Mooring, 9944 Bon Nue Dr., El Cajon, Calif. 92021

[21] Appl. No.: 453,787

[22] Filed: May 30, 1995

[51] Int. Cl.[6] .................................. H04B 1/08; A61F 9/00
[52] U.S. Cl. .................................. 455/90; 455/66; 2/12; 2/181.4
[58] Field of Search .................. 455/66, 89, 90, 455/95, 100, 344, 351; 2/10, 410, 417, 908, 909, 12, 181.4, 918, 422

[56] References Cited

U.S. PATENT DOCUMENTS

| | | | |
|---|---|---|---|
| 3,492,582 | 1/1970 | Heywood | 455/66 |
| 4,484,029 | 11/1984 | Kenney | 455/89 |
| 4,490,012 | 12/1984 | Magiske | 359/877 |
| 4,520,510 | 6/1985 | Daigle | 2/426 |
| 4,526,473 | 7/1985 | Zahn, III | 368/10 |
| 4,630,317 | 12/1986 | Brown et al. | 2/12 |
| 4,636,866 | 1/1987 | Hattori | 345/8 |
| 4,751,691 | 6/1988 | Perera | 368/10 |
| 4,833,726 | 5/1989 | Shinoda et al. | 455/90 |
| 4,856,089 | 8/1989 | Horton | 2/10 |
| 4,869,575 | 9/1989 | Kubik | 345/8 |
| 4,934,773 | 6/1990 | Becker | 359/214 |
| 5,046,192 | 9/1991 | Ryder | 455/351 |
| 5,101,504 | 3/1992 | Lenz | 455/90 |
| 5,105,475 | 4/1992 | Lynd et al. | 2/10 |
| 5,404,577 | 4/1995 | Zuckerman et al. | 455/66 |
| 5,410,746 | 4/1995 | Gelber | 455/344 |
| 5,438,702 | 8/1995 | Jackson | 455/90 |
| 5,465,421 | 11/1995 | McCormick et al. | 455/351 |

*Primary Examiner*—Reinhard J. Eisenzopf
*Assistant Examiner*—Lester G. Kincaid
*Attorney, Agent, or Firm*—Charles C. Logan, II

[57] ABSTRACT

An elongated panel configured in the shape of a visor has its respective left and right rear edges pivotally secured to the respective left and right ends of a band-shaped support member whose rear surface has a concave curvature to mate with the front of a person's forehead. The vertical orientation of the visor can be adjusted with respect to the band-shaped support member. An elongated strap is secured to the rear surface of the band-shaped support member and it has a plurality of loops secured to its rear surface. A bandanna is threaded through the respective loops and tied at the rear of the wearer's head. A display panel is formed below the visor adjacent its front end and it may have a mirror, a pager, a clock and a battery mounted therein. An audio speaker ear piece may be pivotally mounted adjacent either the left or right edge of the visor. An audio microphone may be pivotally mounted adjacent one of the edges of the visor. A pair of glasses may be supported by structure that is pivotally secured to the left and right edges of the visor. An audio jack is mounted in the visor and it is connected to the microphone and ear pieces. An electrical cord has its one end plugged into the jack and its other end may be connected to an FM transceiver and a cellular phone that may be worn in a shoulder holster by the person wearing the visor.

12 Claims, 2 Drawing Sheets

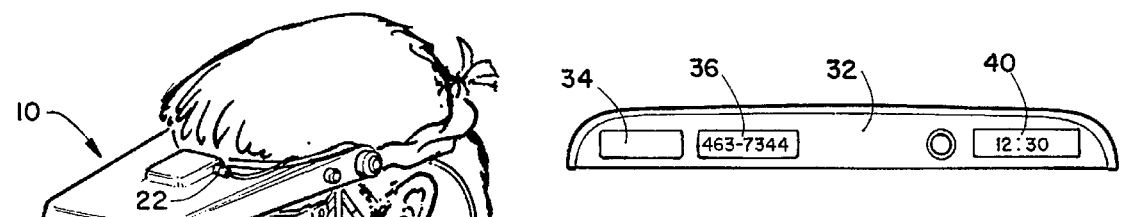
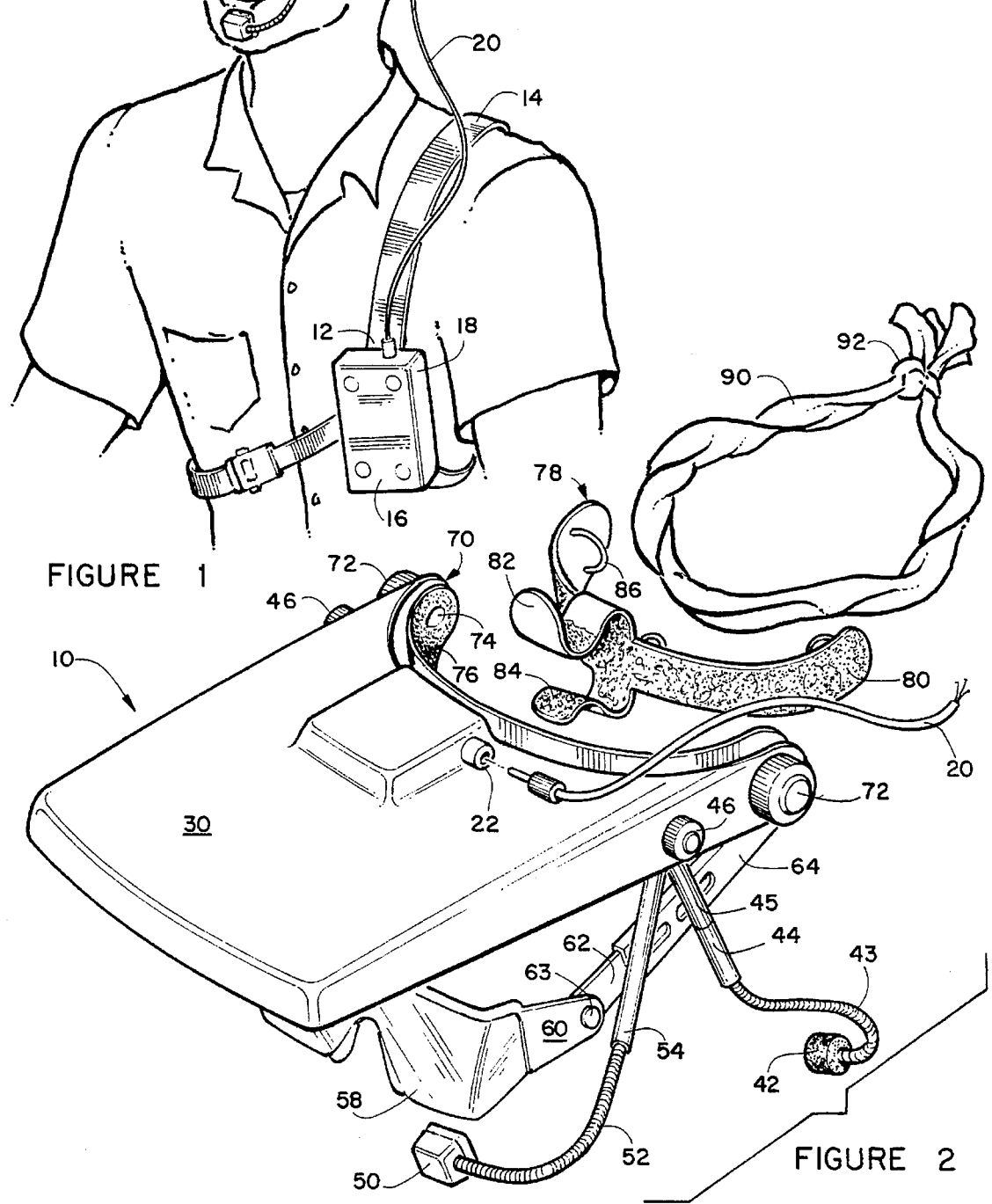

COMMUNICATIONS VISOR

BACKGROUND OF THE INVENTION

The invention relates to a visor to be worn on a person's forehead and more specifically to a novel communications visor.

The secret to safe work in the field for a tree surgeon is communication with his crew. Presently most tree surgeons and their assistants communicate with each other by yelling to each other. This is not an efficient system because when a chipper or other machinery is being used the noise of the machinery interferes with attempts to communicate by voice. Lack of communication means danger on the job. It also results in inefficient use of the tree surgeons time because of stopping to be heard or getting other equipment.

Recently hard hats have been marketed with a transceiver mounted in them. These hats have not been popular because the worker head gets very hot and sweaty while doing his job. As a result, most tree surgeons only wear the hats for a small portion of the time during a job. When the worker takes off his hat he is out of communication with the other workers.

There are numerous other situations where it would be beneficial to have a novel communications visor. For example, a secretary could wear one that would allow her to use its pre-wired microphone and audio to speak with different communications equipment such as a transcriber, a telephone, a pager, a radio, etc. Some other examples would be a dispatcher, the person taking orders at a drive-up window, the crew of a ship, and other people that need to receive communications from co-workers and supervisors. The novel visor also could be used by adults and children to listen to a radio, a tape deck, or a CD player.

It is an object of the invention to provide a novel communications visor that is lightweight and causes relatively little fatigue.

It is also an object of the invention to provide a novel communications visor that can incorporate a rear view mirror to allow the worker to see what is happening behind them.

It is another object of the invention to provide a novel communications visor that can incorporate a pager to keep the worker in touch with telephone calls.

It is a further object of the invention to provide a novel communications visor that incorporates a clock having a LCD display the worker can use to time how long it takes to do a particular job.

It is an additional object of the invention to provide a novel communications visor that can incorporate audio ear piece speakers and an audio microphone that can be connected to an FM transceiver and a cellular phone carried in a shoulder holster by the worker.

It is another object of the invention to provide a novel communications visor that can have its vertical angular orientation adjusted with respect the wearer's head.

It is also an object of the invention to provide a novel communications visor that can be secured to a person's head by a bandanna.

It is an additional object of the invention to provide a novel communications visor that has been pre-wired with audio speakers that can be used to listen to a radio, tape deck, or CD player.

It is another object of the invention to provide a novel communications visor that would be supported on a person's head by a headband that is removable and washable.

It is a further object of the invention to provide a novel communications visor that can have its audio speakers and microphone folded up under the bottom surface of the visor when they are not being used.

SUMMARY OF THE INVENTION

The novel communications visor allows tree surgeons and their assistants to maintain constant contact with each other. This allows immediate communication of potential danger from one worker to another. It also allows the workers to be more efficient when working together on a project. The communications visor additionally allows the workers to initiate and also receive telephone calls while on the job while working either up in a tree or in a bucket or on the ground.

The communications visor is preferably made of plastic material that is lightweight. A display panel is formed on the inside of the visor adjacent its front end. Various items, such as a mirror, a pager having a LCD display, a clock having a LCD display and a battery may be mounted therein. A left and a right ear piece audio speaker is pivotally mounted adjacent the respective left and right edges of the visor. These speakers are supported by telescoping arm structure and the speakers may be stored when not in use in cavities in the bottom surface of the visor. An audio microphone is also pivotally secured to one of the edges of the visor. It is supported in telescoping structure and when not in use it can be stored in a cavity formed in the bottom surface of the visor. Additionally, a set of support arms may be pivotally secured to the respective left and right edges of the visor and the front ends of these support arms would removably receive the temples of a pair of glasses or sunglasses. The temples have structure which allows the lenses to be pivoted upwardly out of the wearer's view when so desired.

The electrical circuitry for the various communications components is incorporated into the plastic structure of the visor. A jack would be mounted on the visor for receiving an electrical wire that would connect to an FM transceiver and/or cellular phone that would be carried by the worker in a shoulder holster.

The rear end of the visor has its respective left and right ends pivotally secured to the respective left and right ends of an elongated band-shaped support member. Positive angular rotation can be accomplished using any conventional well known structure. The rear surface of the band-support member has a concave configuration to mate with the forehead of the person wearing the visor. Also secured to the rear surface of the band-like support member is a strip of hook fastening material (Velcro) that mates with a strip of loop material (Velcro) on the front surface of a strap. Additional hook and loop fastener tabs can also be secured vertically. The rear surface of the strap has a plurality of loops attached thereto. A bandanna is threaded through the loops and the wearer can tie a knot at the rear of his head to secure the bandanna in place. The strip of fastening material and the bandanna can be easily removed for washing when they become wet, sweaty or dirty. A worker would normally have a couple of spare strips of fastening material and a couple of spare bandannas on him.

Uses for the novel communications visor are unlimited. A common requirement would be applications when a person needs to be available for quick communications with their office, their customers, their family, their co-workers and their supervisors.

DESCRIPTION OF THE DRAWINGS

FIG. 1 is a front perspective view illustrating a person wearing the novel communications visor;

FIG. 2 is an exploded front perspective view of the novel communications visor;

FIG. 3 is a rear elevation view of the display panel extending downwardly from the bottom surface of the visor adjacent its front end;

DESCRIPTION OF THE PREFERRED EMBODIMENT

Figure 4:
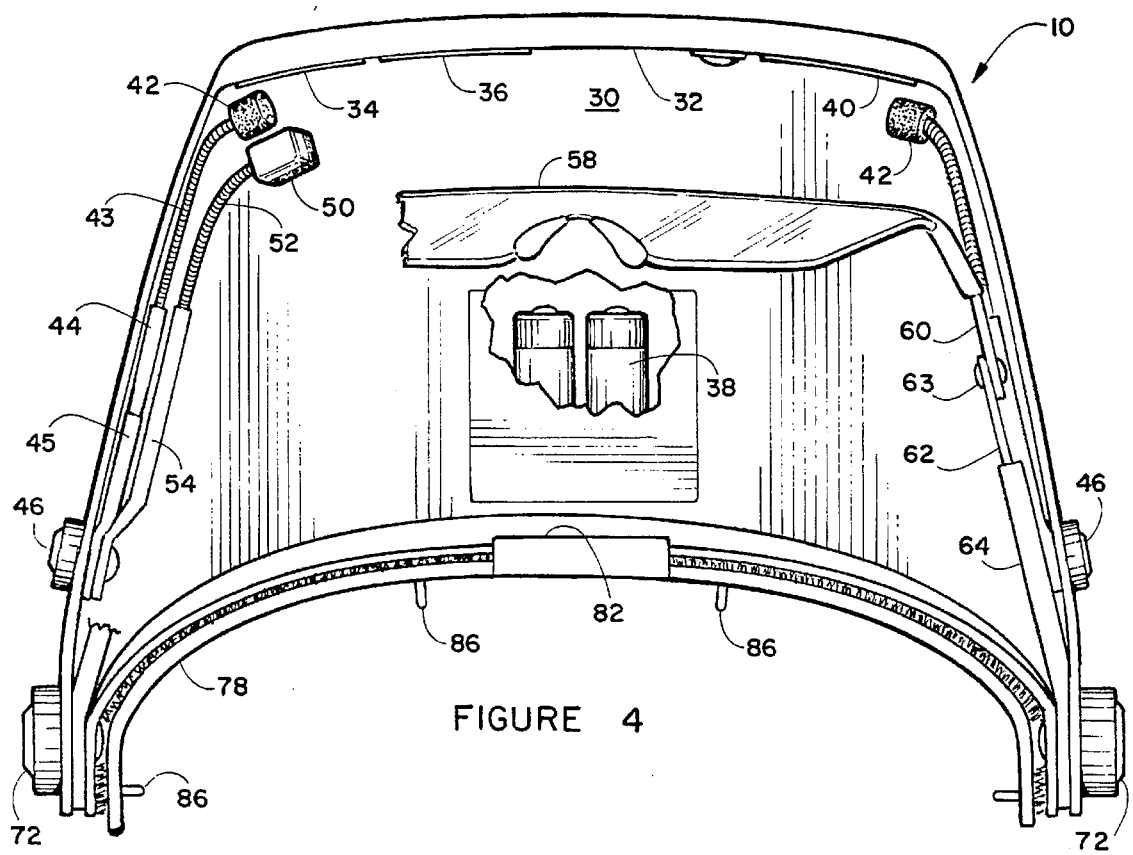
FIG. 4 is a bottom plan view of the novel communications visor.

The novel communications visor will now be described by referring to FIGS. 1–5 of the drawings. The visor is generally designated numeral 10 and the manner in which it is worn is illustrated in FIG. 1. The user may wear a holster 12 attached to a strap 14. A cellular phone 16 and an FM transceiver 18 may be carried in the holster. An electrical cord 20 has its other end plugged into a jack 22 mounted in the visor.

The specific structure of the visor is best understood by referring to FIGS. 2–4. The basic structure of the visor is an elongated panel 30 that is preferably formed of molded plastic. A display panel 32 extends downwardly from the bottom surface of panel 30 adjacent its forward end. A mirror 34, a pager 36 having an LCD display, a battery 38 and a clock 40 having a LCD display may be mounted in the display panel.

An earpiece audio speaker 42 is connected to a bendable length of material 43 whose rigid end portion 44 is telescopically received in tubular member 45. The rear end of tubular member 45 is pivotally mounted on pin 46 and one of these ear piece audio speakers may be pivotally mounted on each side of the visor. When not in use, these ear piece audio speakers can be stored in recesses formed in the bottom surface of panel 30 or screwed thereto by suitable attachment structure.

Microphone 50 is mounted on the bottom end of a flexible, bendable member 52 and its top end is telescopically mounted in tubular sleeve 54. The top end of tubular sleeve 54 is also mounted on pivot pin 46. When not in use, microphone 50 may be swiveled upwardly and captured in a recess formed in the bottom surface of panel 30 or secured thereto by suitable attachment structure.

A pair of glasses 58 that may be sunglasses or reading glasses, have a left and a right support arm 60. The rear of support arms 60 are pivotally attached to the front ends of temple member 62 by a pin 63. Temple 62 is telescopically received in tubular sleeve 64 whose top end is also pivotally mounted on pivot pin 72. Temples 62 can be removed from tubular sleeves 64 when the worker wants to clean his glasses. Also when not in use, the glasses 58 can be pivoted upwardly and secured by suitable attachment means.

The structure for supporting the visor 10 on a person's head is best illustrated in FIGS. 2 and 4. The rear end of panel 30 has a concave rear edge. Spaced rearwardly therefrom is an elongated band-shaped support member 70. Knobs 72 are mounted on pins 74 passing through the respective left and right rear ends of panel 30 and also the respective left and right ends of support member 70.

Figure 5:
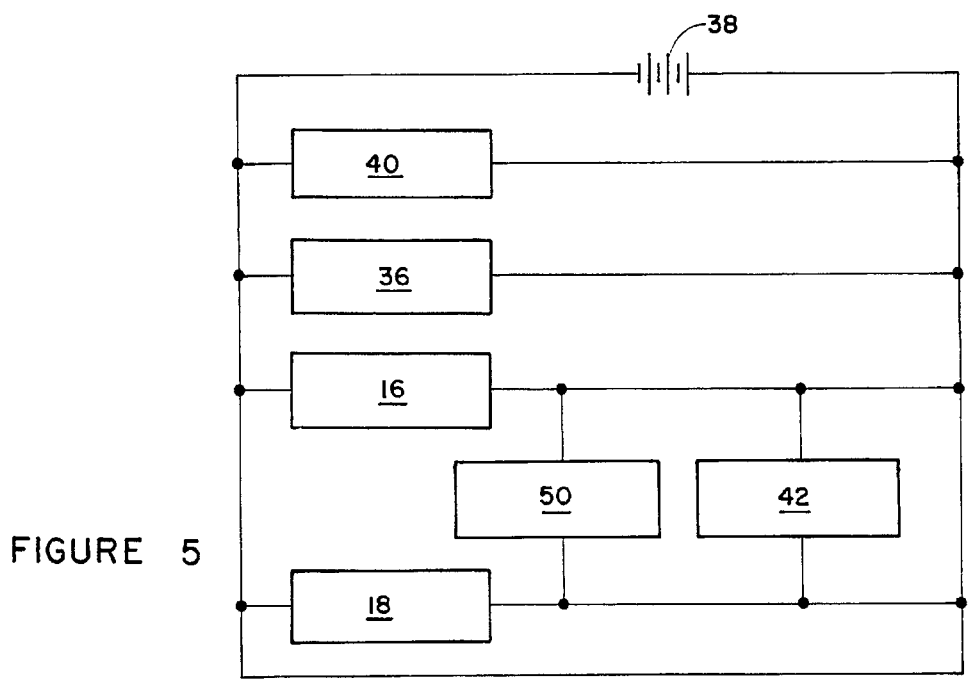
FIG. 5 is a schematic electrical diagram of the electrical circuit for the communications visor.

The rear surface of support member 70 has a concave curvature similar to that of a person's forehead and it has hook and loop material 76 glued thereon. Visor 70 may be adjusted vertically with respect to support member 70 and locked in various angular orientations by conventional well known structure. An elongated fabric strap 78 has hook and loop fastening material 80 on its front surface that mates with hook and loop material 76. A top tab 82 and a bottom tab 84 of hook and loop material can also be attached around the height of support member 70 to positively secure it in place. A plurality of loops 86 are secured to the back rear surface of strap 78. A bandanna 90 is threaded through the respective loops and tied in a knot 92 at the rear of the head of the person wearing the visor. Electrical cord 20 may be captured in bandanna 90 so that it is out of the way and doesn't get caught on adjacent structure. Bandanna 90 and strap 78 are both washable and replaceable when they have gotten dirty and sweaty. FIG. 5 is a schematic diagram of the electrical circuit for the communications visor 10.

What is claimed is:

1. A communications visor comprising:

an elongated panel configured in the shape of a visor to be worn adjacent a person's forehead to shield a person's eyes from the sun, said panel having a front edge, a rear edge, a left edge, a right edge, a top surface and a bottom surface;

an elongated support member having a left end, a right end, a front surface, a rear surface, a top edge and a bottom edge; said rear surface having a concave curvature that faces rearwardly toward a person's forehead when it is worn; the respective left and right ends of said elongated support member being secured to the respective left and right edges of said elongated panel adjacent its rear end;

an elongated cloth member and means for securing said cloth member to said elongated support member so that said communications visor can be secured to the wearer's head; and said means for securing said cloth member to said elongated support member comprises an elongated flexible strap, seperate from but releasably secured to said elongated cloth member, and having a front surface and a rear surface; hook and loop fastener material is secured to the rear surface of said elongated support member and hook and loop fastening material is secured to the front surface of said flexible strap to detachably secure said elongated flexible strap to the rear surface of said elongated support member.

2. The communications visor as recited in claim 1 wherein said elongated cloth member is a bandanna.

3. The communications visor as recited in claim 2 further comprising a plurality of loops secured to the rear surface of said flexible strap and said bandanna is threaded therethrough.

4. The communications visor as recited in claim 1 further comprising means for adjusting the vertical orientation of said elongated panel with respect to said elongated support member.

5. The communications visor as recited in claim 1 further comprising:

a mirror having a reflective surface;

a clock having a face; and means for mounting said mirror and clock to the bottom surface of said elongated panel with the reflective surface of the mirror and the face of the clock facing rearwardly toward a person's face.

6. The communications visor as recited in claim 1 further comprising a battery and means for supporting said battery on the bottom surface of said panel.

7. The communications visor as recited in claim 1 further comprising:
   a pager having a face; and
   means for mounting said pager to the bottom surface of said elongated panel with the face of the pager facing rearwardly toward a person's face.

8. The communications visor as recited in claim 1 further comprising at least one ear piece audio speaker and means pivotally securing it to said elongated panel.

9. The communications visor as recited in claim 1 further comprising an audio microphone and means pivotally securing it to said elongated panel.

10. The communications visor as recited in claim 1 wherein said visor further defines an audio jack and further includes:
   an FM transceiver and means for electrically connecting it to said audio jack.

11. The communications visor as recited in claim 1 wherein said visor further defines an audio jack and further comprises:
   a cellular phone and means for connecting it to said audio jack.

12. The communications visor as recited in claim 1 further comprising a pair of glasses having a left support arm and a right support arm and means connecting said respective left and right support arms to the respective left and right edges of said elongated panel.

* * * * *